(12) United States Patent
Cuffe et al.

(10) Patent No.: US 7,506,546 B2
(45) Date of Patent: Mar. 24, 2009

(54) DIGITAL LOG AMPLIFIER FOR ULTRASONIC TESTING

(75) Inventors: John Michael Cuffe, Reedsville, PA (US); Klaus Peter Busch, Rodenbach (DE); Scott Allen Herbster, Middleburg, PA (US)

(73) Assignee: GE Inspection Technologies, LP, Lewistown, PA (US)

( * ) Notice: Subject to any disclaimer, the term of this patent is extended or adjusted under 35 U.S.C. 154(b) by 0 days.

(21) Appl. No.: 12/104,871

(22) Filed: Apr. 17, 2008

(65) Prior Publication Data

US 2008/0202244 A1    Aug. 28, 2008

Related U.S. Application Data

(63) Continuation of application No. 11/266,854, filed on Nov. 4, 2005, now Pat. No. 7,389,692.

(51) Int. Cl.
*G01N 29/06* (2006.01)
*G01N 29/44* (2006.01)
*A61B 8/08* (2006.01)
*A61B 8/00* (2006.01)

(52) U.S. Cl. ............... 73/602; 600/437; 600/443
(58) Field of Classification Search ............ 73/602
See application file for complete search history.

(56) References Cited

U.S. PATENT DOCUMENTS

| | | | | |
|---|---|---|---|---|
| 5,373,741 A | * | 12/1994 | Volkmann et al. | 73/602 |
| 6,063,033 A | * | 5/2000 | Haider et al. | 600/447 |
| 6,932,770 B2 | * | 8/2005 | Hastings et al. | 600/443 |
| 6,997,875 B2 | * | 2/2006 | Brock-Fisher et al. | 600/443 |
| 2004/0059218 A1 | * | 3/2004 | Kanda et al. | 600/437 |

* cited by examiner

*Primary Examiner*—Hezron Williams
*Assistant Examiner*—Rose M Miller
(74) *Attorney, Agent, or Firm*—Marjama Muldoon Blasiak & Sullivan LL

(57) ABSTRACT

The invention provides an ultrasonic object inspection system for measuring the physical properties of a test object which includes a pulse generator for sending an electrical pulse signal to a transducer. The transducer then applies an ultrasonic signal to the test object and receives an ultrasonic echo signal from the test object which is then converted by the transducer to an electrical echo signal for sending to a signal processing circuit. The signal processing circuit includes a plurality of signal processing paths with each path scaling the electrical echo signal to a different degree and including a respective analog to digital converter for converting the electrical echo signal to a digital electrical echo signal. The signal processing circuit further includes a logic circuit for selecting the output of the respective analog to digital converter that provides the digital echo signal having the greatest amplitude without exceeding a predetermined saturation threshold.

5 Claims, 3 Drawing Sheets

DIGITAL LOG AMPLIFIER FOR ULTRASONIC TESTING

CROSS-REFERENCE TO RELATED APPLICATIONS

This application is a continuation of U.S. patent application Ser. No. 11/266,854, filed Nov. 4, 2005.

FIELD OF THE INVENTION

The present invention is directed to a method and system for processing acoustic signals for use in ultrasonic inspection and testing, and more particularly to simultaneously processing an acoustic signal with multiple linear amplifiers to obtain a combined linear digital output signal having a dynamic response range that is greater than the individual ranges of the amplifiers.

BACKGROUND OF THE INVENTION

Ultrasonic inspection employs high frequency, ultrasonic waves generated by a transducer to examine test objects and make measurements. Ultrasonic inspection can be used for detection of flaws in test objects, and for performing evaluation, dimensional measurements, material characterization, and more on objects. Measurement procedures initially developed for metals have been extended to engineered materials such as composites, where such characteristics as anisotropy and inhomogeneity are of concern. Advances in digitization and computing capabilities have changed the types of instruments and algorithms that are used in processing the resulting data. High-resolution imaging systems and multiple measurement modalities for characterizing a flaw have emerged. Of interest are detecting, characterizing, and sizing defects, as well as characterizing the materials in which they are found. The objectives of ultrasonic testing range from the determination of fundamental microstructural characteristics such as grain size, porosity, texture and preferred grain orientation, to material properties related to failure mechanisms such as fatigue, creep, and fracture toughness.

In ultrasonic testing, a transducer containing a piezoelectric element is excited by an electrical pulse to transmit an ultrasonic pulse into a test object. The sound wave propagates through the test object and is reflected. The transducer receives the reflected wave and the reflected wave is converted by the transducer into an electrical signal and analyzed to determine whether a discontinuity exists in the test object. A flaw or discontinuity in the test object is characterized by certain anomalous profiles in the electrical signal that are viewable on an analog display, such as an oscilloscope or a recording device.

The electrical signal from a transducer representing the reflected sound wave must be amplified for input into a display or recording device. In order to be displayed, the amplified signal must fall within a certain dynamic response range that is defined by the maximum and minimum operating parameters of the respective display device. In many cases, the signal representing the acoustic wave includes multiple components. For example, in the case of a flaw occurring near the surface of an object, the echo caused by the near-surface defect is received within the interval of the initial pulse. In that case the flaw is not detectable by a visual display, or a recording device, since the amplitude of the echo is small relative to the initial pulse. Since the instrument receives them concurrently, the relatively small-magnitude echo signal from the near-surface flaw is essentially superimposed on the larger initial pulse or interface signal. The large difference in amplitude of the two simultaneous signals makes the smaller signal very difficult to detect.

Previously, analog logarithmic amplifiers have been used in attempts to compress the dynamic response range, but analog amplifiers are not particularly well suited to perform this due to the limited bandwidth and dynamic response range of analog logarithmic amplifiers. Analog techniques are limited by noise and accuracy problems.

Therefore there is a need for a device for digitally processing simultaneous ultrasonic signals having widely varying amplitudes and combining them for display into a continuous linear digital signal having a wide dynamic range.

SUMMARY OF THE INVENTION

The apparatus and method of the present invention provides a plurality of linear amplifiers simultaneously processing an ultrasonic signal. Each amplifier of the plurality of linear amplifiers has a predetermined gain level suitable for achieving the desired output signal level for input to an analog to digital (A/D) converter for processing. The output of each amplifier is sampled by each respective A/D converter at a very high frequency to convert the analog signal output of each of the linear amplifiers to a digital signal. Logic circuits simultaneously monitor all of the output digital signals from the A/D converters. The logic circuits determine which output of the A/D converters has the greatest linear output and stores the selected output in a memory storage device. The saved output waveforms are subsequently combined into a continuous linear digital output that has a dynamic response range that is approximately the sum of the individual dynamic response ranges of the individual A/D converters. The combined continuous linear digital output waveform may be accurately converted by corresponding computing to logarithmic scaling to produce a waveform having a wide dynamic range comparable to the output of a logarithmic amplifier.

An advantage object of the present invention is that the device can detect small defects near the surface of a test object by eliminating the constant wave signal reflected from the top surface of the test object and detecting the small signals that are normally masked by the constant wave signal reflected from the top surface.

Another advantage of the present invention is that simultaneous reflected waveforms can be measured and recorded having a wide dynamic response range with no distortion of the respective waveforms.

Yet another advantage of the present invention is that a wide dynamic response range is provided for the measurement of signals reflected from various depths in a material characterized by high signal attenuation.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

Wherever possible the same reference numbers will be used throughout the drawings to refer to the same or like parts.

DETAILED DESCRIPTION OF THE INVENTION

Figure 1:
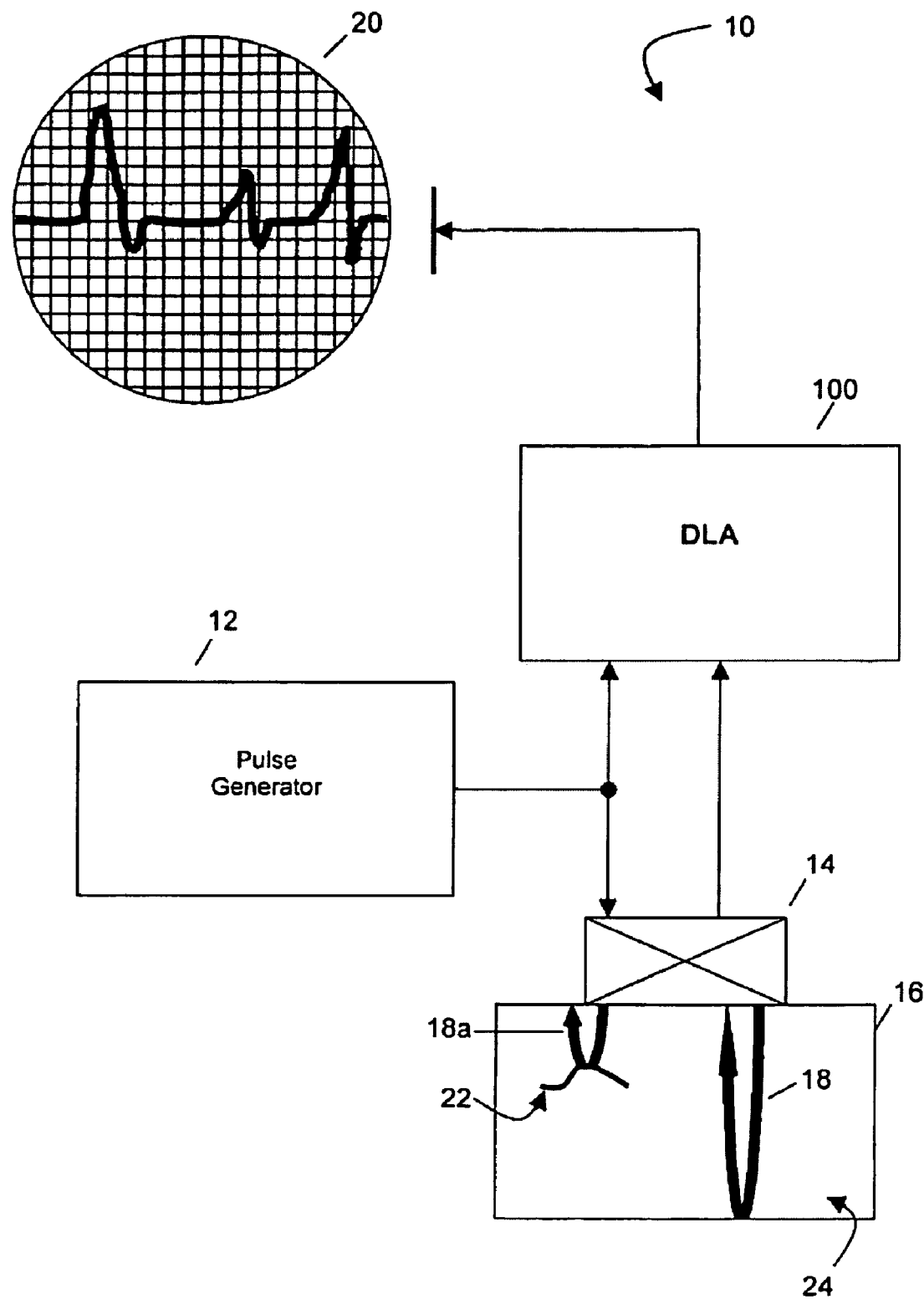
FIG. 1 is a schematic diagram of a test arrangement using the digital log amplifier of the present invention.

Referring to FIG. 1, a test inspection arrangement 10 includes a pulse generator circuit 12 that transmits a pulse to a transducer 14 for propagating an ultrasonic acoustic wave 18 through a test object 16. Wave 18 is reflected back to the transducer 14. In the example shown in FIG. 1, one transducer both transmits and receives the acoustic wave, however, other test configurations may also be employed with multiple transducers, some that transmit, some that receive, and some that perform both transmitting and receiving functions. The transducer 14 receives the reflected acoustic wave and converts it back into an electrical signal, which is input to the digital log amplifier (DLA) 100 of the present invention. The DLA 100 processes the electrical signal representing the reflected waveform, as discussed in further detail below. The output waveform of the DLA 100 is displayed on an oscilloscope 20 or other similar peripheral display or storage device (not shown). Many other test arrangements may be substituted for the arrangement of FIG. 1, as are well known to those skilled in the art. The arrangement of FIG. 1 is therefore presented as an example, and the invention is not limited to the particular arrangement of this example.

As indicated in FIG. 1, a defect 22 in the test object 16 will reflect the waveform 18 at a point different from a backwall 24 of the test object 16, resulting in different wave propagation times that may be shown on the screen of the oscilloscope 20. The smaller the defect 22, the smaller the magnitude of the reflected wave, so that in some instances, the sensitivity of the output device or the non-linearity of the amplifier, may cause a small reflected signal to be lost. Also, where the defect 22 is very near to the surface, the reflected wave 28 associated with the defect 22 may be received by the amplifier and output to the display 20 at approximately the same time as the initial pulse 26 or the interface signal. When displayed on an analog display the initial pulse 26 is very large in relation to the near-surface reflected wave 28, the small reflected signal 28 is also lost in the larger waveform.

Figure 2:
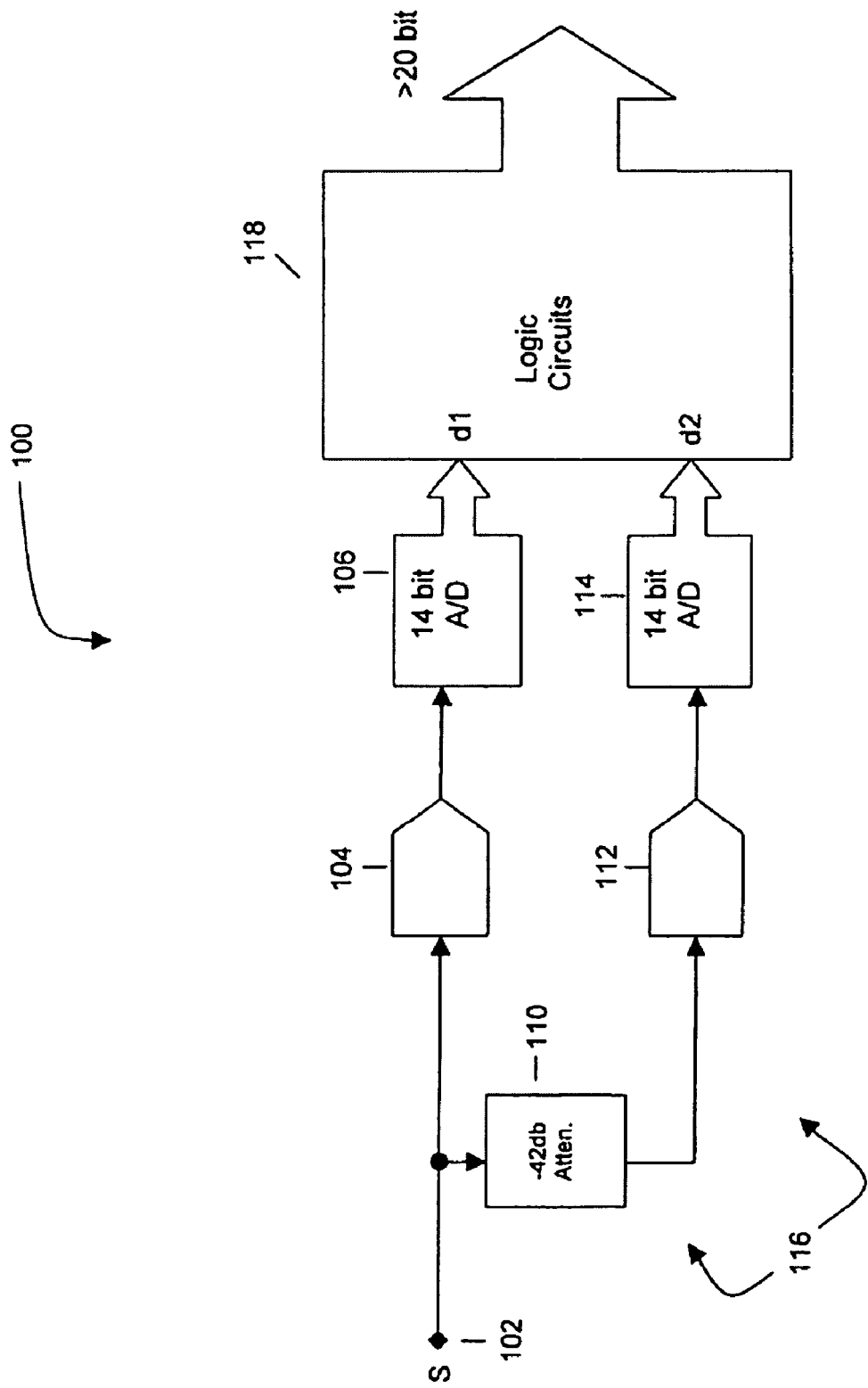
FIG. 2 is a schematic diagram of the digital log amplifier.

Referring to FIG. 2, signal S representing a reflected waveform propagated through a test object is applied to the input 102 of the DLA 100. An amplifier 104 has a gain suitable for processing the unattenuated signal S, and amplifies the signal S for input to an analog-to-digital (A/D) converter 106. Preferably, all of the A/D converters used in the present invention are 14-bit converters with a high-dynamic response range but the invention can principally perform on each type of analog to digital (A/D) converter. The output of amplifier 104 is inserted into the A/D converter 106 and sampled at a very high rate, to provide a digitized representation, $d.sub.1$, of the analog signal S. The sampling frequency must be at least twice that of the analog signal frequency, and preferably in practice should be at least three times the frequency of analog signal S. The preferred sampling frequency for low signal frequency applications is around 50 MHz and for high signal frequency applications is around 100 MHz, but may be more or less depending on the frequency of the analog signal S.

Analog signal S is simultaneously processed by at least one attenuators. FIG. 2 illustrates only one attenuation path 116, but it is understood that the DLA 100 of the present invention may typically include multiple parallel paths with different attenuation values. Each attenuation path 116 includes an attenuator 110, an amplifier 112 and an A/D converter 114 connected in series, similar to attenuation path 116. In the example of FIG. 2, attenuator 110 attenuates signal S for input to amplifier 112. Attenuation values are preferably selected in increments of −6 db (e.g., −24 db, −30 db, −36 db, et. seq.), which conveniently correspond to an additional sampling bit for every 6 db of attenuation, however any magnitude of signal attenuation may be substituted if desired. In the example shown in FIG. 2, minus (−) 42 db signal attenuation is provided by the attenuator 110 before amplification. Amplifier 112 has a gain suitable for the dynamic response range of the attenuated signal S for providing a desired output level of the amplified signal. The output of the amplifier 112 is inserted into A/D converter 114 and simultaneously sampled at the same rate as A/D converter 106 to provide a second digitized representation, $d.sub.2$, of the signal S. Any number of attenuator paths may be used to process signal S simultaneously for input to a corresponding number of amplifiers. Attenuation values are selectively assigned to match desired response levels, and each amplifier has a gain level designed with respect to the associated attenuator to provide the desired output signal level for the associated A/D converter.

Logic circuits 118 analyze the signal levels of the digitized outputs d1, d2 of the A/D converters 106, 114 or if additional paths are used the digitized outputs of all paths. The logic circuits 118 determine which of the converters 106, 114 has the greatest output, which is linear, as the amplitude of signal S fluctuates. The logic circuits 118 determine whether the digitized output signal from each converter falls between a predetermined saturation threshold and a predetermined minimum signal level. Those outputs falling outside the desired band are eliminated—i.e., outputs above the predetermined saturation level or below the minimum signal level. The selected converter output waveforms that fall between the saturation threshold and minimum levels are saved to a digital memory storage device (not shown). The saved output waveforms of signals with different amplitudes are subsequently combined by logic circuits 18 to form a continuous linear digital output for display on an oscilloscope 20 or other peripheral device connected to the amplifier output. At each sample point, $N.sub.1$, $N.sub.2$, $N.sub.3$ etc., which occur every 20 nanoseconds at 50 MHz sample rate, the outputs from multiple A/D converters are available. Thus for sample point $N.sub.1$, logic circuits 18 decide which output is within range and this amplitude is used in the logic circuit output. Next for sample point $N.sub.2$, logic circuits 18 decide which A/D output to use in the logic circuit output. This process is continued for each sample point. Every 6 dB of attenuation (approximately) at the input to the 14-bit A/D converter 114 corresponds to an extra bit of sensitivity and a doubling of response range of the resulting logic circuit output signal. The dynamic response range of the resulting logic circuit output signal is greater than 20-bit, which corresponds with the sum of the multiple dynamic response ranges of individual amplifier and A/D converter combinations. The digitized signal may be converted to a logarithmic scaling by a corresponding conversion algorithm implemented in the logic circuits 18 for compressing the dynamic response range of the combined output signal to a screen or recorder presentation. This conversion algorithm produces logarithmic output that is more accurate over a greater dynamic range than can be produced by existing techniques.

Figure 3:
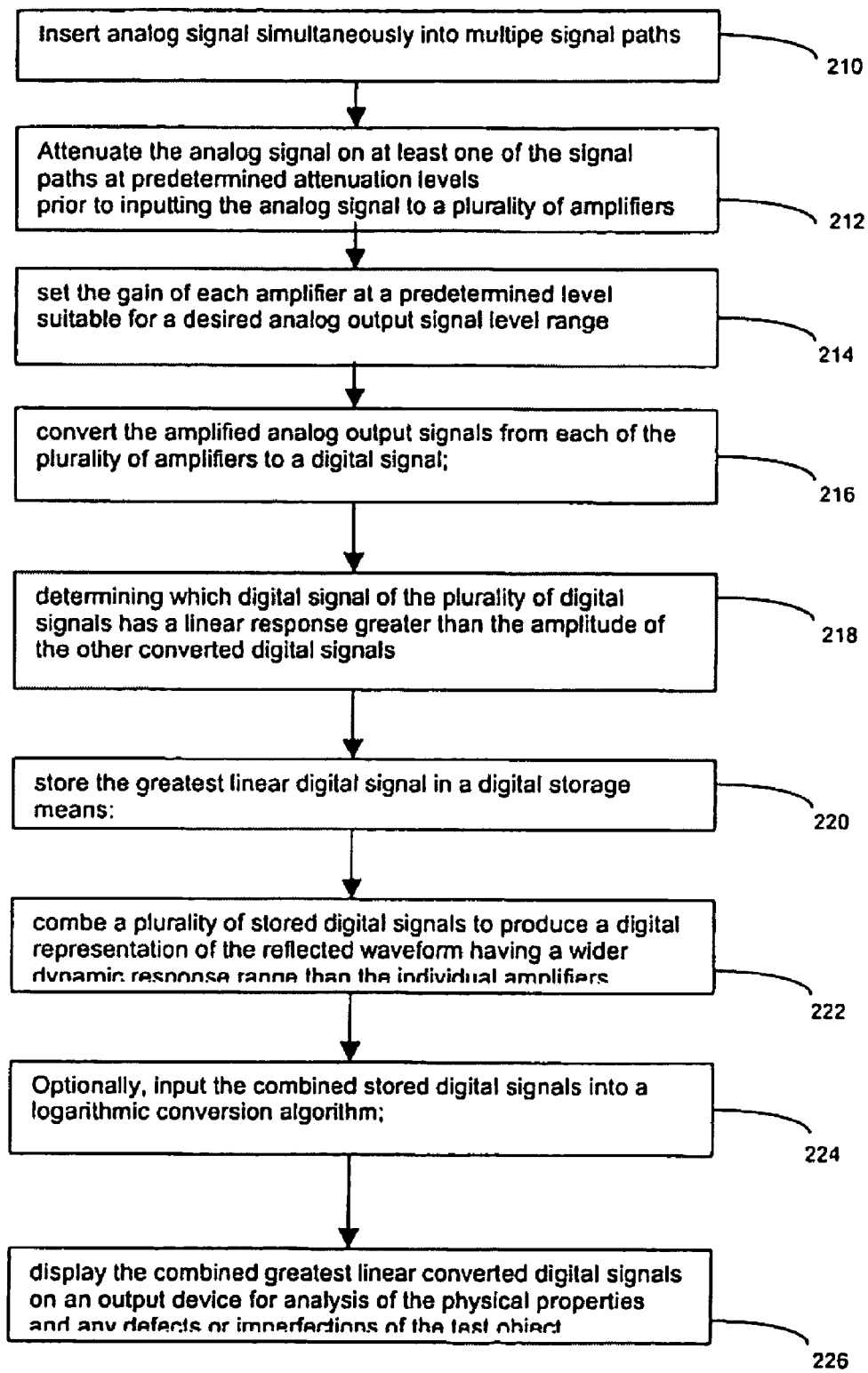
FIG. 3 is a flow chart of the method of converting an analog signal into a plurality of digital components representing a reflected ultrasonic waveform.

The method, for converting an analog signal into a plurality of digital components representing a reflected ultrasonic waveform for testing objects, is set forth in FIG. 3. The flowchart, generally designated 200, begins at step 210, processing a reflected analog signal by amplifying the analog signal simultaneously through a plurality of different amplifiers. Then, at step 212, the analog signal is attenuated at a plurality of predetermined attenuation levels prior to inputting the analog signal to at least one of the plurality of amplifiers. Next, at step 214, the gain of each of the plurality of amplifiers is set at a predetermined level suitable for a desired predetermined analog output signal level range. At step 216, the amplified analog output signals from each of the plurality of amplifiers are converted to a digital signal. Then, at step 218, the system determines which converted digital signal has a response that is (1) linear and (2) greater than the amplitude of the other converted digital signals. Following step 218, at step 220, that greatest linear converted digital signal is stored in memory or other digital storage means. Then at step 222 a plurality of the stored converted digital signals is combined to produce a digital representation of the reflected waveform, the digital representation of the reflected waveform has a wider dynamic response range than the response range of the separate individual amplifiers. At step 224, which is optional, the combined stored greatest linear converted digital signals is input to a logarithmic conversion algorithm. Then, at step 226, the combined greatest linear converted digital signals are displayed on an output device for analysis of the physical properties and any defects or imperfections of the test object.

It is known that small defects present near the surface of a test object are difficult to detect. The reflected waveform from the near-surface defect is very small, relative to the interface signal or surface reflection. The magnitude of the interface signal may be on the order of one hundred times the magnitude of the signal from the defect. Thus the larger signal overloads the amplifier, and the signal from the defect is contained within the larger waveform signal and is lost or undetectable. The interface may be subtracted from the amplifier output, since the magnitude and waveform of the interface signal is known. By eliminating the interface signal, smaller signals such as the near-surface flaw are selectively displayed, allowing the tester to obtain more accurate inspection results of near-surface defects. Also, where ultrasonic inspection techniques are employed to measure thickness of a test object, wide variations in amplitude may be eliminated by capturing the waveforms over a wide dynamic response range, allowing greater accuracy in thickness measurements.

Another advantage of the present invention is realized in the ultrasonic inspection of composite components which are characterized by high attenuation. The wide dynamic response range of the DLA permits accurate amplitude measurements of signals from various depths in test objects of composite materials, as well as testing composite objects with wide variations in thickness.

Finally, the DLA allows the combined outputs of the stored waveforms to be easily processed into logarithmic scaling without the noise and accuracy limitations normally associated with the analog logarithmic amplifiers.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. An ultrasonic object inspection system for measuring the physical properties of a test object comprising:
    a pulse generator for generating and transmitting an electrical pulse signal to a transducer;
    said transducer for receiving and converting said electrical pulse signal to an ultrasonic signal, applying said ultrasonic signal to said test object, receiving an ultrasonic echo signal from said test object, and converting said ultrasonic echo signal to an electrical echo signal, and transmitting said electrical echo signal to a signal processing circuit;
    said signal processing circuit for receiving and processing said electrical echo signal;
    said signal processing circuit comprising a plurality of signal processing paths, each of said signal processing paths scaling said electrical echo signal to a different degree and comprising a respective analog to digital converter for converting said electrical echo signal to a digital electrical echo signal; and
    said signal processing circuit further comprising a logic circuit for selecting the output of said respective analog to digital converter that provides the digital electrical echo signal having the greatest amplitude without exceeding a predetermined saturation threshold.

2. The ultrasonic object inspection system of claim 1, further comprising a display for displaying said selected output as a signal representative of said electrical echo signal.

3. The ultrasonic object inspection system of claim 1, wherein each of said plurality of signal processing paths comprises an amplifier.

4. A method of ultrasonic object inspection testing for measuring the physical properties of a test object comprising the steps of:
    generating and transmitting an electrical pulse signal;
    receiving and converting the electrical pulse signal to an ultrasonic signal;
    applying said ultrasonic signal to said test object;
    receiving an ultrasonic echo signal from said test object;
    converting said ultrasonic echo signal to an electrical echo signal;
    transmitting said electrical echo signal;
    receiving and processing said electrical echo signal in a plurality of signal processing paths;
    scaling said electrical echo signal to a different degree in each of said signal processing paths;
    converting said electrical echo signal to a digital electrical echo signal in each of said signal processing paths; and
    selecting the digital electrical echo signal having the greatest amplitude without exceeding a predetermined saturation threshold.

5. The method of ultrasonic object inspection testing of claim 4, further comprising the step of converting said selected digital electrical echo signal to a logarithmic scale to compress the amplitude of the continuous linear digital waveform over a wide dynamic range.

* * * * *